US005788287A

United States Patent [19]
Gremel

[11] Patent Number: 5,788,287
[45] Date of Patent: Aug. 4, 1998

[54] OUTLET CONNECTOR FOR OXYGENATOR

[75] Inventor: Robert F. Gremel, Huntington Beach, Calif.

[73] Assignee: Medtronic, Inc., Minneapolis, Minn.

[21] Appl. No.: 591,240

[22] Filed: Jan. 17, 1996

[51] Int. Cl.[6] .................................................. A61M 1/03
[52] U.S. Cl. .............................. 285/13; 285/924; 285/14; 285/125.1; 422/46
[58] Field of Search ..................... 128/DIG. 3; 422/46; 285/13, 14, 150, 152, 153, 154, 924, 125.1, 127.2, 129.1, 129.2

[56] References Cited

U.S. PATENT DOCUMENTS

| 2,981,072 | 4/1961 | Brewington | 285/13 |
|---|---|---|---|
| 3,693,657 | 9/1972 | Olson | 285/14 |
| 3,856,333 | 12/1974 | Cox | 285/14 |
| 3,958,425 | 5/1976 | Marosinak | 285/14 |
| 4,138,288 | 2/1979 | Lewin | 128/DIG. 3 |
| 4,519,393 | 5/1985 | Elgas et al. | 285/355 |
| 4,521,038 | 6/1985 | Cerny | 285/24 |
| 4,603,890 | 8/1986 | Huppee | 285/14 |
| 4,619,640 | 10/1986 | Potolsky et al. | 604/7 |
| 5,096,233 | 3/1992 | Dlouhy | 285/154 |
| 5,174,610 | 12/1992 | Svendsen et al. | 285/13 |
| 5,270,005 | 12/1993 | Raible | 422/46 |

FOREIGN PATENT DOCUMENTS

| 0 089 122 | 9/1993 | European Pat. Off. | A61M 1/03 |
|---|---|---|---|
| 1287655 | 8/1962 | France . | |
| 1514437 | 2/1968 | France | 285/14 |
| 43 44 403 A1 | 10/1994 | Germany | A61M 16/06 |
| 125983 | 1/1960 | U.S.S.R. | 285/14 |
| 439291 | 1/1975 | U.S.S.R. | 422/46 |
| WO 93/03787 | 3/1993 | WIPO | A61M 39/04 |

Primary Examiner—Eric K. Nicholson
Attorney, Agent, or Firm—Harold Patton; Peter Forrest; Curtis D. Kinghorn

[57] ABSTRACT

The present invention is an outlet connector configuration for an oxygenator that prevents excessively high positive or negative pressure from forming in the oxygenator and helps to minimize the possibility of misidentifying the outlet connector. The outlet connector is hollow and substantially cylindrically tubular in shape so that a hollow inner conduit is formed. The outlet connector is in fluid communication with the outlet manifold of an oxygenator through the inner conduit. In one embodiment, the outlet connector has an elongated hole extending through the tubular material of the outlet connector into the hollow inner conduit formed therein. The elongated hole is preferable large enough to be felt by the fingers of the person connecting tubing to the outlet connector. The elongated hole is preferably arrow shaped with the arrow pointing in the direction of fluid flow out of the outlet manifold. In an alternate embodiment, the outlet connector has a channel formed in the outer surface of the outlet connector. The channel extends from the distal end of the outlet connector opposite the point of connection of the outlet connector to the oxygenator towards the oxygenator. The channel does not extend entirely through the tubular material making up the wall of the outlet connector but instead extends into the wall material from the exterior surface only a fraction of the thickness of the wall material.

27 Claims, 9 Drawing Sheets

OUTLET CONNECTOR FOR OXYGENATOR

BACKGROUND OF THE INVENTION

1. Field of the Invention

The invention relates to devices for infusing and removing gases from blood and more particularly relates to an outlet connector for connecting a means to remove gases from a device for infusing and removing gases from blood to a device for infusing and removing gases from blood.

2. Description of Related Art

During cardiac surgery, it is often desirable to maintain circulation of blood through a patient's body. This is often done by connecting a patient to an extra-corporeal system that adds oxygen to and removes carbon dioxide from the blood, heats or cools the blood and provides impetus to the blood to cause the blood to circulate through the patient's vascular system.

Devices, typically called oxygenators such as that shown in FIG. 1 generally labeled 2, serve the function of adding oxygen to the blood and removing carbon dioxide from the blood. Most oxygenators operate by imparting oxygen to and removing carbon dioxide from blood passing through the extra-corporeal circuit through transfer of carbon dioxide to and oxygen from a gas.

Many current oxygenators use a group of porous fibers arranged in a fiber bundle 4 as conduits for the gas used to transfer the oxygen to and carbon dioxide from the blood in the extra-corporeal circuit. In a typical design for oxygenator 2, individual fibers in fiber bundle 4 are surrounded by blood taken from a patient. The blood is removed from the venous side of a patient and is pumped through the oxygenator 2 over the fibers and is then infused into the patient's arterial side.

The venous blood from the patient has a relatively low amount of oxygen and a relatively high amount of carbon dioxide. As the blood passes through the oxygenator 2, the blood acquires oxygen from and gives up carbon dioxide to the oxygenator 2.

The typical oxygenator 2 operates by diffusing oxygen from gas in the interior passages of fibers in fiber bundle 4 through the walls of the fibers into the blood and by diffusing carbon dioxide from the blood through the walls of the fibers in the fiber bundle 4 into the interior passages of fibers in fiber bundle 4. The fibers of fiber bundle 4 are relatively porous to diffusion of oxygen and carbon dioxide across the walls of the individual fibers.

Because the partial pressure of oxygen in the gas in the fibers is higher than the partial pressure of oxygen in the blood, oxygen diffuses through the walls of the fibers from the gas in the interior of the fibers to the blood. Conversely, because the partial pressure of carbon dioxide in the blood is higher than the partial pressure of carbon dioxide in the gas in the fibers, carbon dioxide diffuses through the walls of the fibers from the blood to the gas in the interior of the fibers.

In most current oxygenators 2, the fiber bundle 4 is typically cylindrical with the individual fibers open at each end of the fiber bundle 4. Manifolds at each end of the fiber bundle 4 direct gas into and out of the fiber bundle 4 from a source of gas and to a line to vent the exhaust gas, respectively. An inlet manifold 6 at one end of the fiber bundle 4 directs gas from a source of oxygen rich gas to the open ends of the fibers in fiber bundle 4. Inlet manifold 6 has an inlet connector 8 for connecting the inlet manifold 6 to the source of oxygen rich gas.

An outlet manifold 10 is located at the end of the fiber bundle 4 opposite inlet manifold 6. Gas that has passed through the fiber bundle 4 when the oxygenator 2 is operating will have relatively higher levels of carbon dioxide and relatively lower levels of oxygen than the gas entering the fiber bundle 4. Outlet manifold 10 collects this gas that has passed through the fiber bundle 4 and directs it to a line to vent the exhaust gas.

Outlet manifold 10 has an outlet connector 12 for connecting the outlet manifold 10, through tubing, to the waste gas receptacle. Outlet connector 12 is typically hollow, substantially cylindrical and in fluid communication with outlet manifold 10. This allows a piece of tubing 14 to be connected over the outer surface 16 of outlet connector 12 so that gas can flow out of outlet manifold 10 through the hollow outlet connector 12 and through the interior of the tubing 14 to the waste gas receptacle.

Gas rich in oxygen and low in carbon dioxide enters the inlet manifold 6 through inlet connector 8, passes through the fiber bundle 4 and exits the oxygenator 2 through outlet manifold 10 and ultimately through outlet connector 12.

There are two main problems with the known outlet connectors 12. First, in order to ensure that waste gas is moved out of the oxygenator 2, the outlet connector 12 is typically connected to a source of vacuum pressure (not shown) through tubing 14 to collect and dispose of the gas. But, because the vacuum source is a negative pressure, it is possible to transfer the negative pressure to the gas in the oxygenator 2 and in particular to the gas in the fibers of the fiber bundle 4.

When the gas in the oxygenator 2 has a negative pressure, the partial pressure of oxygen in the fibers of fiber bundle 4 is reduced. Because the partial pressure of oxygen is reduced, the partial pressure differential between the oxygen in the gas in the fibers and the oxygen in the blood is reduced. As a result, less oxygen will pass from the gas to the blood thereby making the oxygenator 2 less efficient and effective as an artificial lung.

An additional problem with a negative gas pressure in the fibers of the fiber bundle 4 is that blood plasma will be pulled from the blood into the fibers thereby clogging the fibers. Clogged fibers prevent the transmission of oxygen or carbon dioxide through the clogged fibers thus making the oxygenator 2 less efficient. Further, blood plasma that is pulled into the fibers becomes damaged. These two problems with negative gas pressure are to be avoided.

A second major problem with the outlet connector 12 is that the outlet connector 12 may be mistaken for one of the other connectors on the oxygenator 2 such as are typically found. If the outlet connector 12 is mistaken for one of the other connectors, one of the operating room personnel may close the outlet connector 12 by capping it.

This problem of misidentification of outlet connector 12 is acerbated where, as commonly occurs, a heat exchanger for heating and cooling the blood passing through the oxygenator 2 is attached to or is formed in the same housing as the oxygenator 2. Heat exchangers that operate by using water to cool or heat the blood will also have at least an inlet and an outlet connector that can also be confused with outlet connector 12.

Where outlet connector 12 has been misidentified and mistakenly capped, oxygen rich gas may be applied under pressure to the oxygenator 2 through the inlet connector 8. However, because outlet connector 12 is capped, the gas will not be able to leave the oxygenator 2 through the outlet connector 12. In this case, the gas pressure in the inside the fibers in the fiber bundle 4 may rise to the input pressure of the gas at inlet connector 8. This may cause the gas under pressure in the interior of the fibers in fiber bundle 4 to be diffused across the fiber walls into the blood which is at a lower pressure. Once in the blood, this pressurized gas will expand and possibly cause embolistic problems.

Both problems of having a gas in the interior of the fibers in fiber bundle 4 that has excessively high or low pressure are to be avoided. FIG. 2 shows one way that these problems have been dealt with in the past. FIG. 2 shows an outlet connector 12 connected to an oxygenator 2. At least one small hole 18 is formed from the outer surface 16 of outlet connector 12 to the interior hollow passage (not shown). Hole 18 vents the interior hollow passage of the outlet connector 12, and consequently the interior of the oxygenator 2, to ambient pressure.

Another solution to the problem of excessively high or low gas pressure in the interior of the fibers of the fiber bundle 4 has been to place small holes in the outlet manifold 10 to vent gas pressure in the outlet manifold 10 to ambient pressure.

Although either of these approaches to solving the problem of excessively high or low gas pressure in the interior of the fibers of the fiber bundle 4 helps to prevent excessively high or low pressure in the interior of the fibers of the fiber bundle 4, neither approach helps to solve the problem of misidentifying the outlet connector 12 mentioned above.

SUMMARY OF THE INVENTION

The present invention is an outlet connector configuration for an oxygenator that prevents excessively high positive or negative pressure from forming in the oxygenator and helps to minimize the possibility of misidentifying the outlet connector. The outlet connector is hollow and substantially cylindrically tubular in shape so that a hollow inner conduit is formed. The outlet connector is in fluid communication with the outlet manifold of an oxygenator through the inner conduit. The outlet connector is shaped to allow tubing to be fluidly connected to it so that gas can flow from the inner conduit through the tubing.

In one embodiment, the outlet connector has an elongated hole extending through the tubular material of the outlet connector into the hollow inner conduit formed therein.

The elongated hole is preferable large enough to be felt by the fingers of the person connecting tubing to the outlet connector. The elongated hole is preferably arrow shaped with the arrow pointing in the direction of fluid flow out of the outlet manifold.

In an alternate embodiment, the outlet connector has a channel formed in the outer surface of the outlet connector. The channel extends from the distal end of the outlet connector opposite the point of connection of the outlet connector to the oxygenator towards the oxygenator. The channel does not extend entirely through the tubular material making up the wall of the outlet connector but instead extends into the wall material from the exterior surface only a fraction of the thickness of the wall material.

In either embodiment of the invention, when tubing is placed over the outlet connector, the tubing should not be placed entirely over the hole or the channel. Instead, at least the proximal end of the hole or channel should be exposed to the atmosphere to allow venting of the inner conduit of the outlet connector to the atmosphere.

It is a primary object of the invention to provide an outlet connector that prevents either excessive negative or positive gas pressure in the oxygenator.

It is another object of the invention to provide an outlet connector that indicates the direction of gas flow out of the oxygenator.

It is another object of the invention to provide an outlet connector that minimizes the possibility of misidentifying the outlet connector.

These and other objects of the invention will be clear with reference to the attached drawings and the following detailed description of the invention. Throughout this description, like elements, wherever referred to, are referenced by like reference numbers.

DETAILED DESCRIPTION OF THE INVENTION

Figure 1:
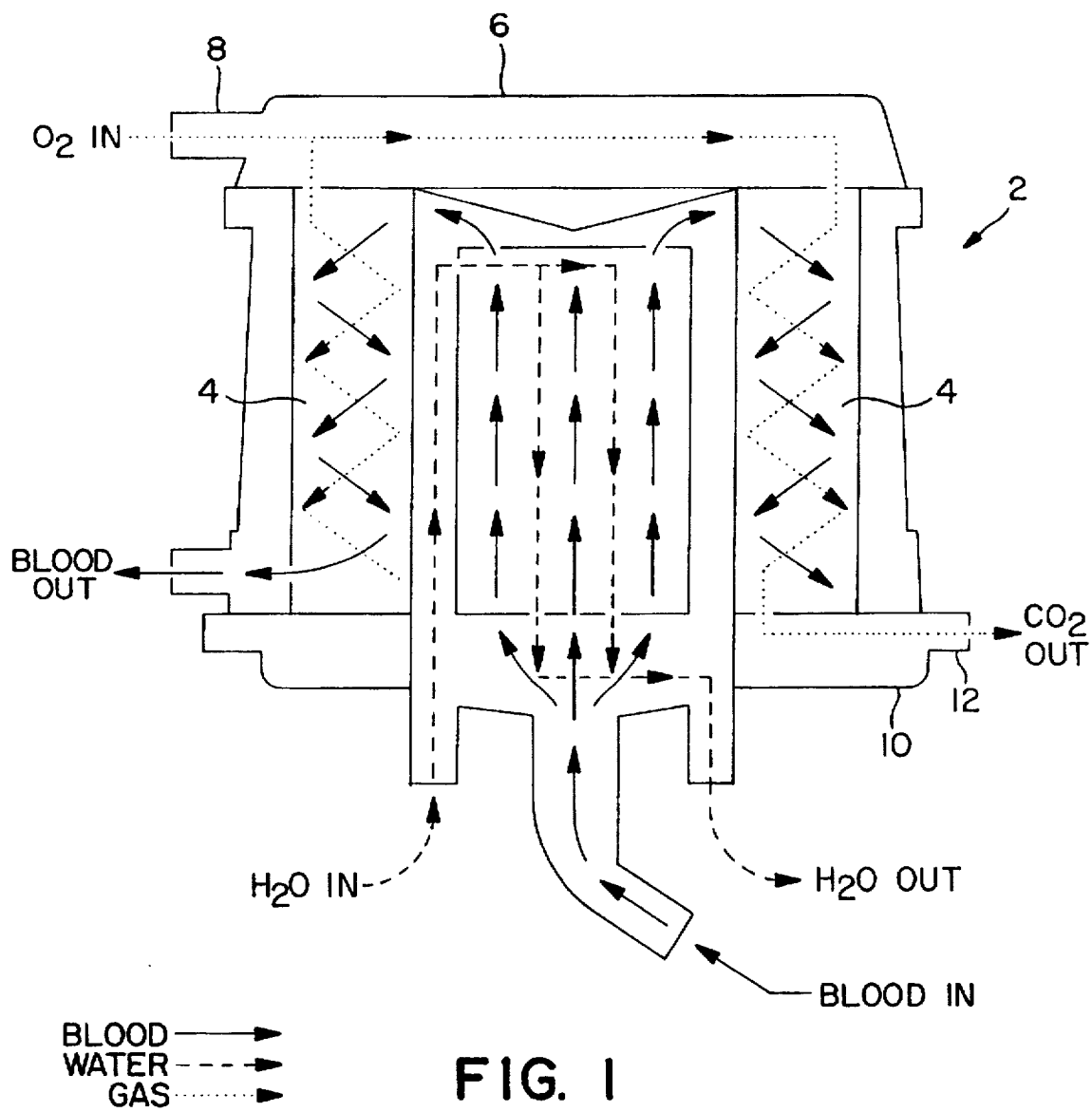
FIG. 1 is a side cross-sectional view of an oxygenator showing the outlet connector.
Figure 2:
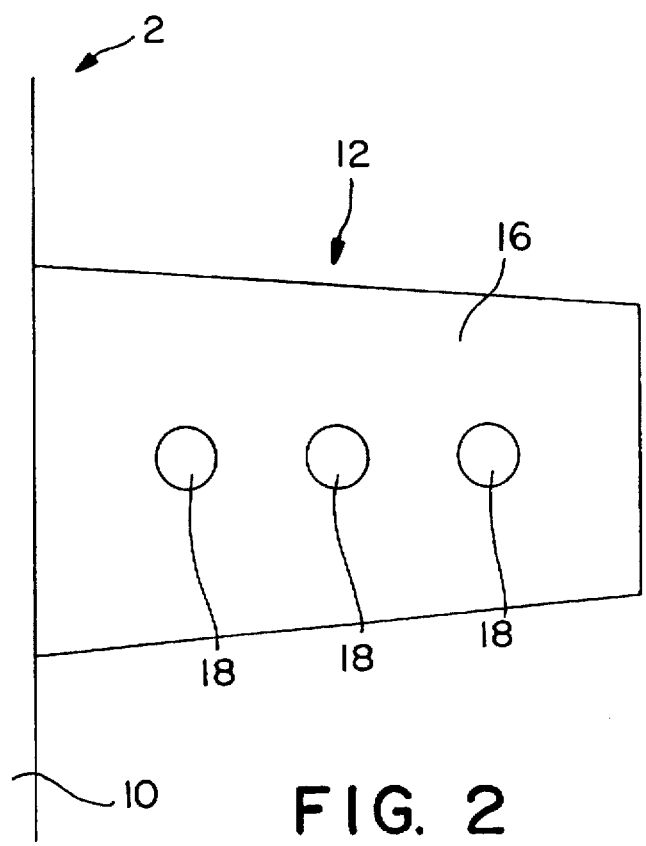
FIG. 2 is a plan view of a prior art outlet connector.
Figure 3:
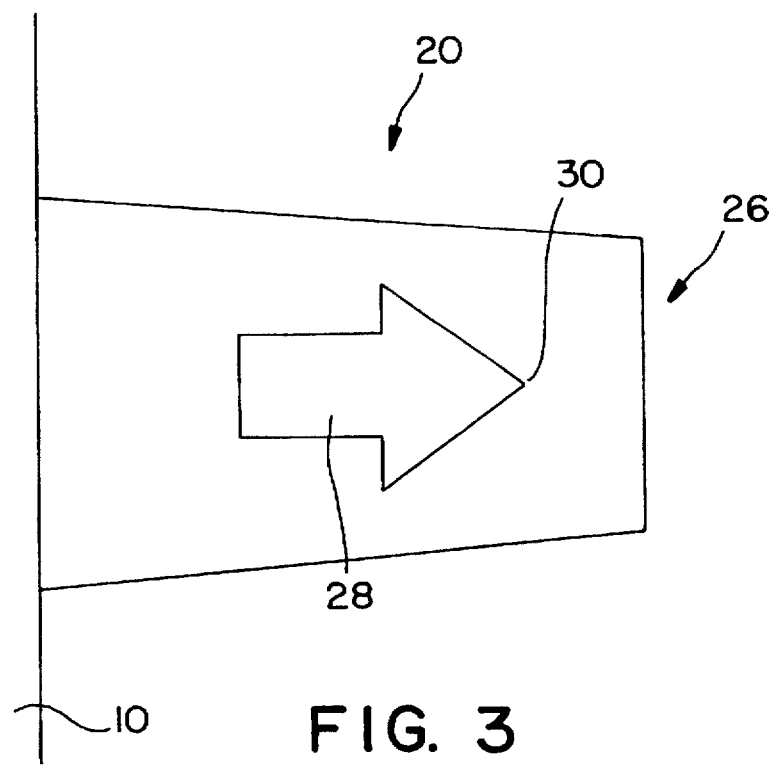
FIG. 3 is a plan view of the outlet connector of the present invention.
Figure 5:
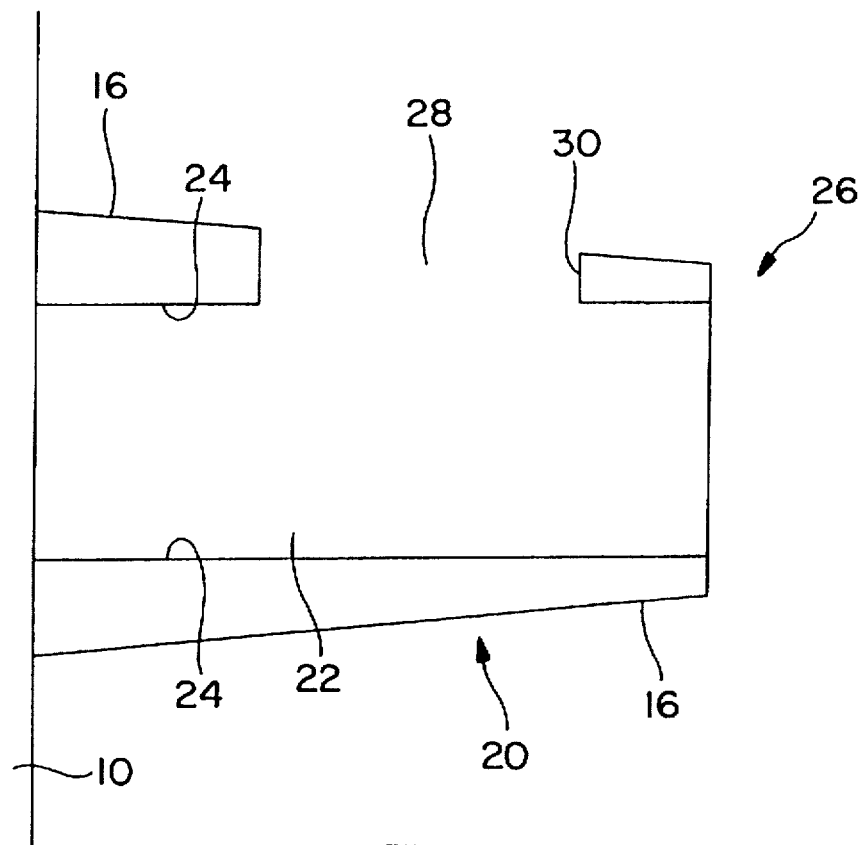
FIG. 5 is a side cutaway view of the outlet connector of FIG. 3.

The connector of the present invention is shown in FIGS. 3 and 5 generally labeled 20 and connected to oxygenator 2. Connector 20 is substantially cylindrical and hollow forming an inner conduit 22. Inner conduit 22 is in fluid communication with outlet manifold 10. Inner conduit 22 is defined by inner surface 24 that is substantially cylindrical and extends from the distal end 26 of connector 20 to outlet manifold 10.

Connector 20 also has an outer surface 16 that is substantially cylindrical. In the preferred embodiment, outer surface 16 tapers slightly from outlet manifold 10 to the distal end 26 of connector 20 to facilitate connecting a piece of tubing 14 to outlet connector 20 as will be described hereafter.

An elongated hole 28 is formed from the outer surface 16 to the inner surface 24 allowing fluid communication between inner conduit 22 and the exterior of the oxygenator 2. Hole 28 is preferably large enough to be felt by the fingers of the person connecting tubing 14 to the outlet connector 20.

In the preferred embodiment shown in FIG. 3, hole 28 is arrow shaped with the tip 30 of the arrow pointing in the direction of gas flow out of oxygenator 2. However, hole 28 may also have other shapes including, but not limited to, oval, square, triangular and rectangular.

Connector 20 is preferably made of a plastic material although it may be made of metal or ceramic materials. Connector 20 may be integrally formed with outlet manifold 10 or may be formed separately and connected directly to outlet manifold 10 by any means such as is well known in the art.

Figure 4:
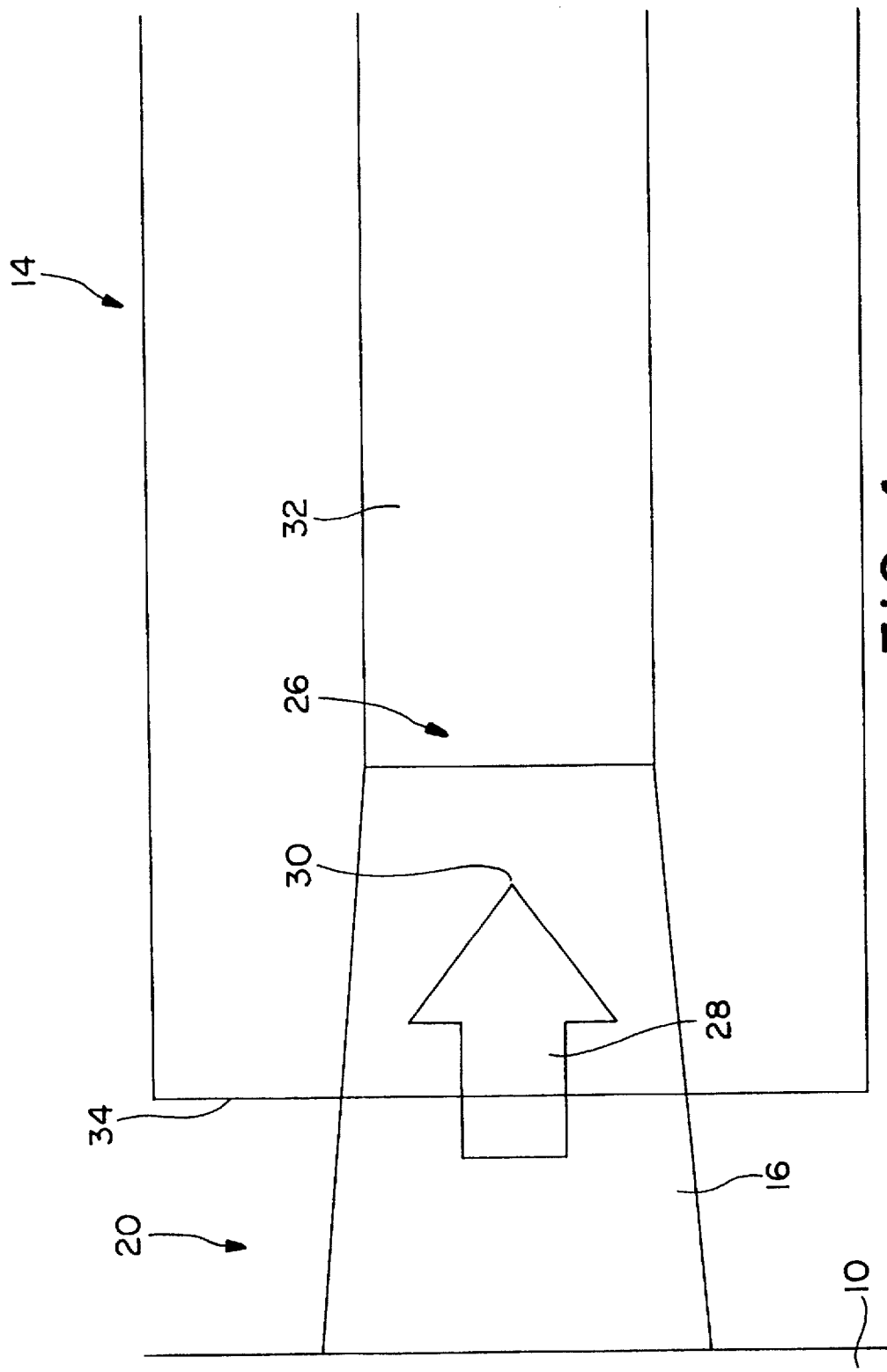
FIG. 4 is a plan view of the outlet connector of FIG. 3 with a piece of tubing attached to it.

In use, a piece of tubing 14 is connected to outlet connector 20 by sliding the inner lumen 32 of tubing 14 over the outer surface 16 of outlet connector 20. The proximal end 34 of tubing 14 is advanced over the outer surface 16 of outlet connector 20 a sufficient distance to securely connect tubing 14 to outlet connector 20 by frictional force but not so far that proximal end 34 completely covers hole 28 (FIGS. 4 and 6).

In the embodiment where hole 28 is arrow shaped, the visual presentment of the arrow indicates to the person attaching tubing 14 to outlet connector 20 that outlet connector 20 is an outlet connector with fluid flowing in the direction that the arrow is pointing. This is a safety feature that helps to prevent the misidentification of outlet connector 20. This helps to prevent the accidental capping of outlet connector 20 or the accidental connection of a piece of tubing to outlet connector 20 that would be inappropriate and that could cause improper operation of the oxygenator and therefore possible harm to the patient.

Additionally, because hole 28 is large enough to be felt by the person connecting tubing 14 to the outlet connector 20 and is elongated, the person connecting the tubing 14 will be able, by tactile sensation alone, to identify outlet connector 20 and distinguish it from the other connectors extending away from a typical oxygenator. This is particularly helpful where an oxygenator and heat exchanger are housed in the same or adjacent containers.

Figure 6:
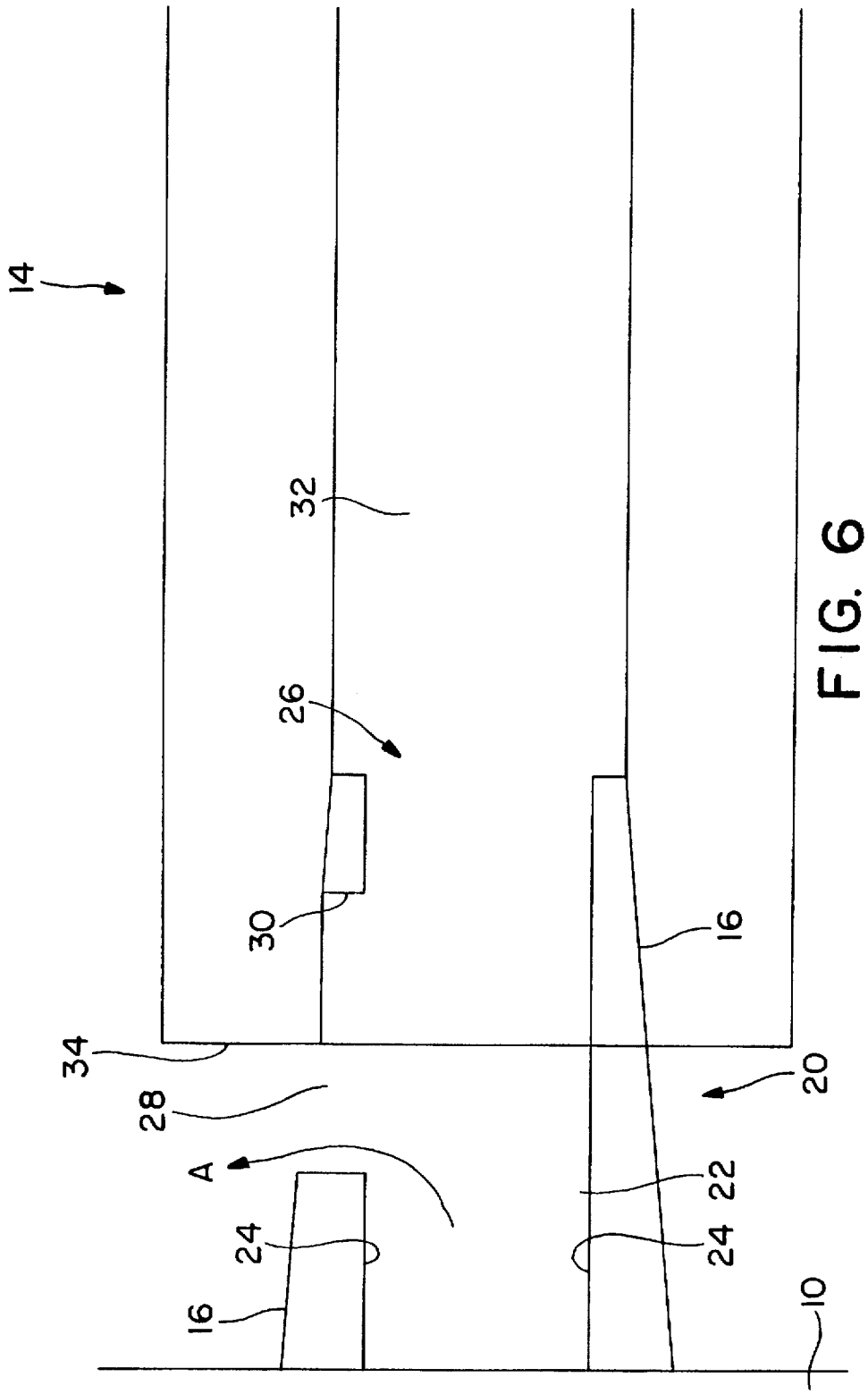
FIG. 6 is a side cutaway view of outlet connector of FIG. 3 and the piece of tubing shown in FIG. 4.
Figure 7:
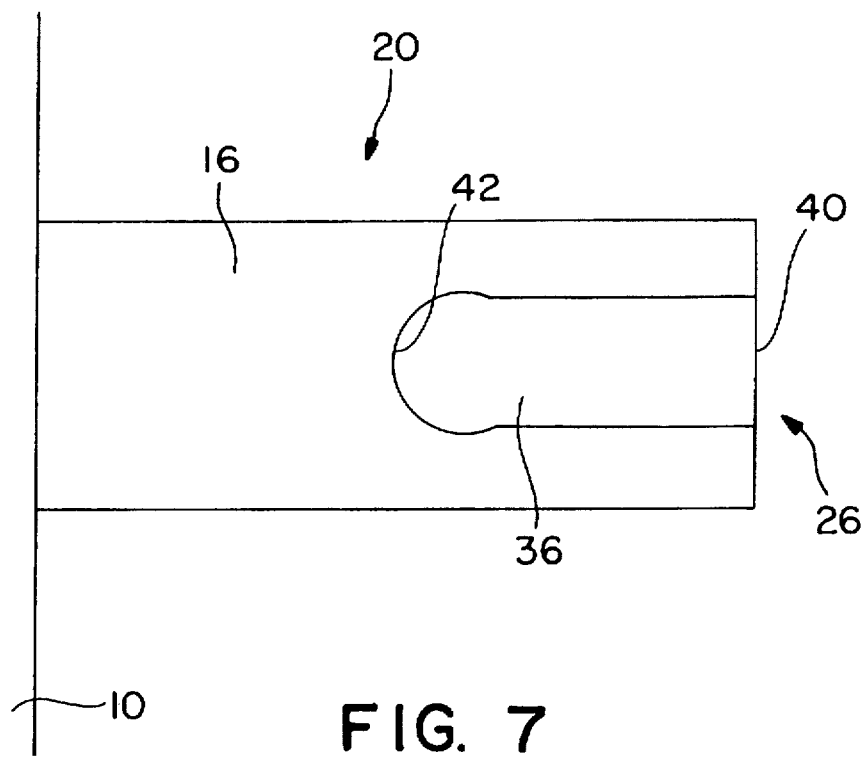
FIG. 7 is a plan view of an alternate embodiment of the invention.

In this way, as shown in FIG. 6, if excessive positive gas pressure is present in inner conduit 22, the excessive positive gas pressure will be vented to the exterior of the oxygenator 2 by passing through hole 28 along the path labeled "A". Likewise, if excessive negative gas pressure is present in conduit 20, the excessive negative gas pressure will be vented to the exterior of the oxygenator 2 by passing through hole 28 also along the path labeled "A".

Figure 8:
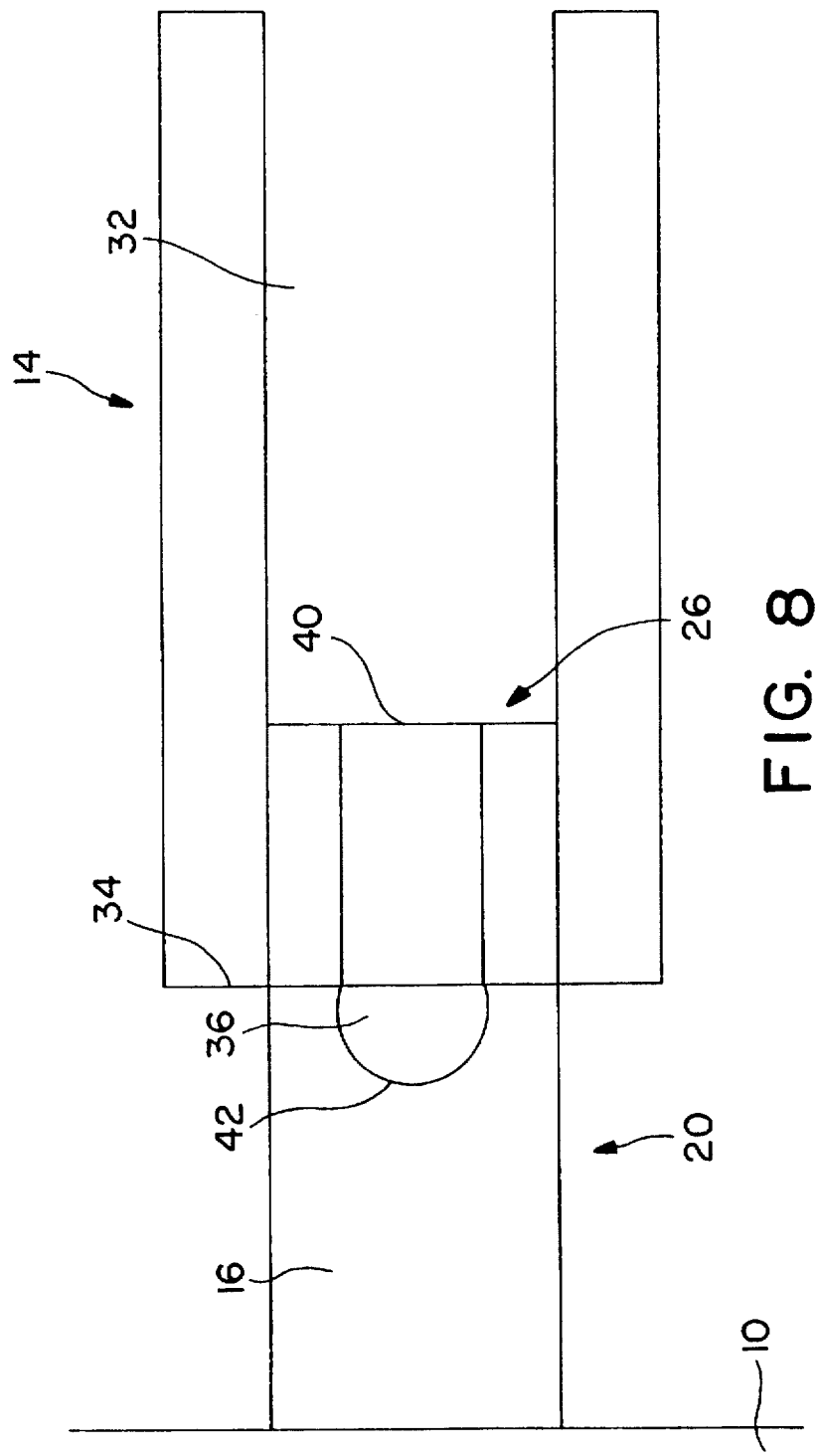
FIG. 8 is a plan view of the invention shown in FIG. 7 with a piece of tubing attached to it.
Figure 9:
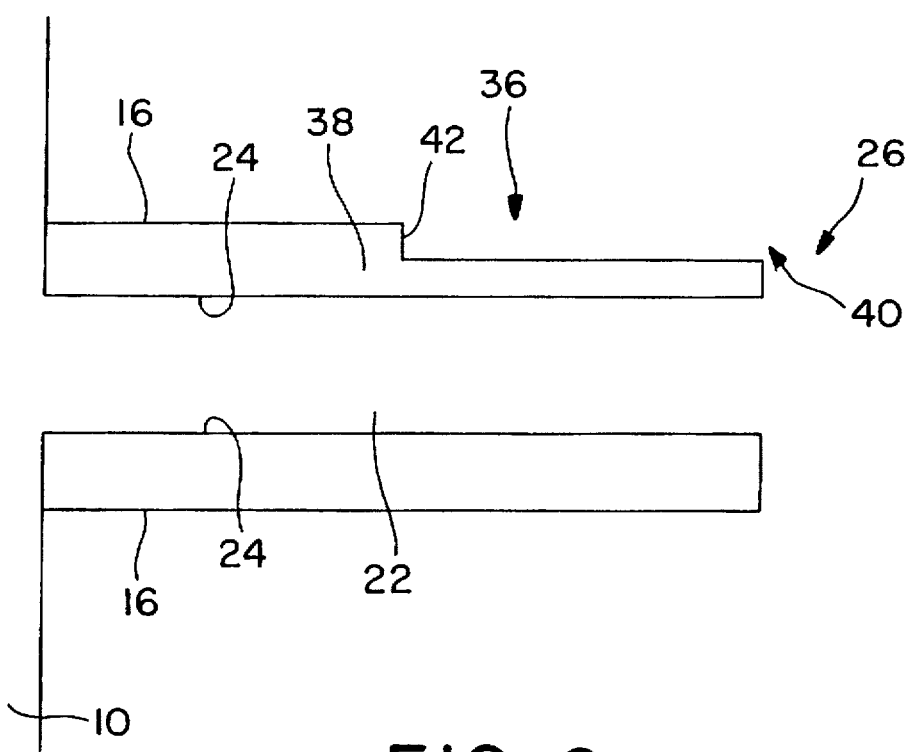
FIG. 9 is a side cutaway view of the invention of FIG. 7.

FIGS. 7–10 show an alternate embodiment of the outlet connector 20. In this embodiment, instead of hole 28, a channel 36 is formed that does not extend entirely from the outer surface 16 to the inner surface 24 of outlet connector 20. Instead, as shown in FIG. 9, channel 36 extends a distance into the material 38 forming outlet connector 20. Channel 36 extends distally to the distal end 26 of outlet connector 20 so that a distal end 40 is formed on channel 36. Channel 36 also has a proximal end 42.

Channel 36 is preferable elongated and more preferably is rectangular shaped with rounded corners. However, channel 36 but may also have other configurations including, but not limited to, circular, oval, triangular, square or arrow shaped.

In addition, channel 36 preferably extends distally to the distal end 26 of outlet connector 20. However, channel 36 may terminate some distance proximal to the distal end 26. In this embodiment, a hole from the distal end of channel 36 may extend to the inner conduit 22 through the inner surface 24. In this way, a fluid path is created from the inner conduit 22 through the hole through the inner surface 24 to channel 36.

Figure 10:
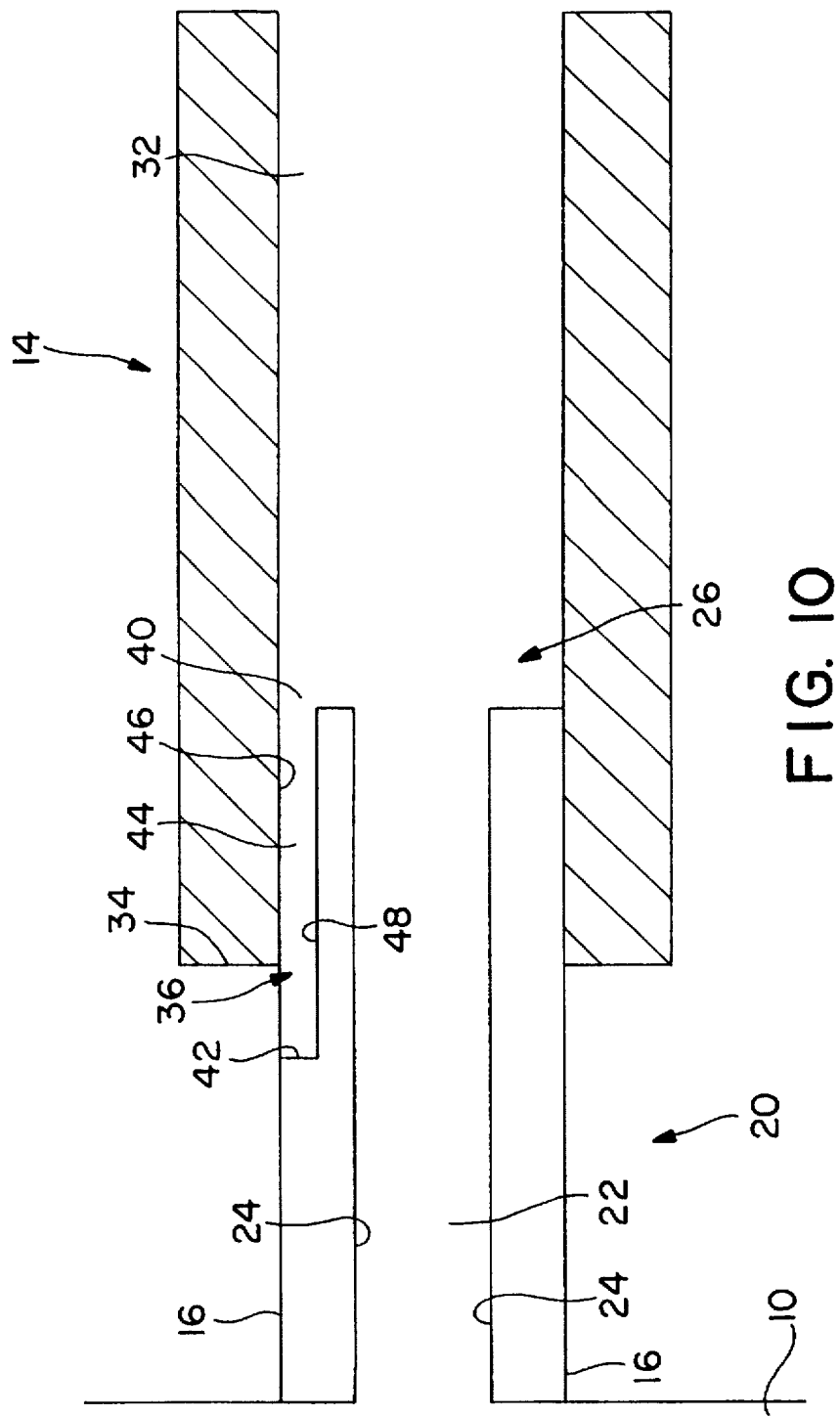
FIG. 10 is a side cutaway view of the invention of FIG. 7 with a piece of tubing attached to it.

In use as above, a piece of tubing 14 is placed over the outer surface 16 of outlet connector 20 so that the tubing 14 is connected to outlet connector 20 by frictional force. However, the proximal end 34 of the tubing 14 should not extend over the proximal end 42 of channel 36 as shown in FIGS. 8 and 10. This forms a passage 44 connecting the distal and proximal ends 40, 42 of channel 36 between the surface 46 forming the boundary of inner lumen 32 of tubing 14 and the surface 48 of channel 36.

In this way, as shown in FIG. 10, if excessive positive gas pressure is present in conduit 20, the excessive positive gas pressure will be vented to the exterior of the oxygenator 2 by passing through the open distal end 40 of channel 36 along passage 44 to the proximal end 42 of channel 36 to the exterior of oxygenator 2. Likewise, if excessive negative gas pressure is present in conduit 20, the excessive negative gas pressure will be vented to the exterior of the oxygenator 2 by passing through the open distal end 40 along passage 44 to the proximal end 42 of channel 36 to the exterior of oxygenator 2.

The invention has been shown and described in connection with a specific embodiment. It is to be realized, however, that the description given herein is for the purpose of illustrating the invention and is not intended to be limiting. It is further understood that improvements and modifications to the disclosure made herein will occur to those skilled in the art and that such improvements and modifications will still fall within the scope of the invention.

I claim:

1. A combination of an oxygenator having an outlet manifold and an outlet connector for connecting the outlet manifold of the oxygenator to tubing so that gas can flow from the outlet manifold through the outlet connector to the tubing, the connector comprising:

a hollow member having a proximal and a distal end, the proximal end of the member connected to the outlet manifold, the member having an outer surface and also having an inner conduit defined by an inner surface, the inner surface extending from the distal end of the member to the outlet manifold so that fluid may flow from the inner conduit to the outlet manifold, the member having a hole formed from the outer surface to the inner surface through which fluid may flow between the inner conduit and the exterior of the oxygenator, the hole being a size to be felt by at least one finger of a person connecting tubing to the outlet connector.

2. The outlet connector of claim 1 in which the hole formed from the outer surface to the inner surface is elongated.

3. The outlet connector of claim 1 in which the hole formed from the outer surface to the inner surface is arrow shaped.

4. The outlet connector of claim 3 in which the hole formed from the outer surface to the inner surface is arrow shaped with the tip of the arrow pointing in the direction of gas flow through the outlet connector.

5. The outlet connector of claim 1 in which the hole formed from the outer surface to the inner surface is oval.

6. The outlet connector of claim 1 in which the hole formed from the outer surface to the inner surface is square.

7. The outlet connector of claim 1 in which the hole formed from the outer surface to the inner surface is triangular.

8. The outlet connector of claim 1 in which the hole formed from the outer surface to the inner surface is rectangular.

9. The outlet connector of claim 1 in which the member is substantially cylindrical.

10. The outlet connector of claim 1 in which the member is integrally formed with the outlet manifold.

11. The outlet connector of claim 1 in which the outer surface of the member is substantially cylindrical.

12. The outlet connector of claim 1 in which the outer surface of the member tapers slightly from the outlet manifold to the distal end of the member.

13. The outlet connector of claim 1 in which the inner surface of the inner conduit is substantially cylindrical.

14. A combination of an oxygenator having an outlet manifold and an outlet connector for connecting the outlet manifold of the oxygenator to tubing so that gas can flow from the outlet manifold through the outlet connector to the tubing, the connector comprising:

a hollow member having a proximal and a distal end, the proximal end of the member connected to the outlet manifold, the member having an outer surface and also having an inner conduit defined by an inner surface, the inner surface extending from the distal end of the member to the outlet manifold so that fluid may flow from the inner conduit to the outlet manifold, the member having a channel formed in the outer surface of the hollow member a distance less than the thickness between the outer and the inner surface, the channel extending proximally from the distal end of the hollow member to the inner surface, so that, when a piece of tubing is placed over the outer surface of the hollow member a distance sufficient to frictionally secure the tubing to the hollow member but not so far as to completely cover the channel, a passage is formed through the channel to vent the inner conduit to the exterior of the oxygenator.

15. The outlet connector of claim 14 in which the channel is elongated.

16. The outlet connector of claim 15 in which the channel is rectangular shaped.

17. The outlet connector of claim 15 in which the channel is circular shaped.

18. The outlet connector of claim 15 in which the channel is oval shaped.

19. The outlet connector of claim 15 in which the channel is triangular shaped.

20. The outlet connector of claim 15 in which the channel is square shaped.

21. The outlet connector of claim 15 in which the channel is arrow shaped.

22. The outlet connector of claim 21 in which the channel is arrow shaped with the tip of the arrow pointing in the direction of gas flow through the outlet connector.

23. The outlet connector of claim 14 in which the member is substantially cylindrical.

24. The outlet connector of claim 14 in which the member is integrally formed with the outlet manifold.

25. The outlet connector of claim 14 in which the outer surface of the member is substantially cylindrical.

26. The outlet connector of claim 14 in which the outer surface of the member tapers slightly from the outlet manifold to the distal end of the member.

27. The outlet connector of claim 14 n which the inner surface of the inner conduit is substantially cylindrical.

* * * * *